United States Patent [19]

Manimaran et al.

[11] Patent Number: 5,191,095

[45] Date of Patent: Mar. 2, 1993

[54] ASYMMETRIC HYDROGENATION OF OLEFINIC AMIDES USING ORGANORUTHENIUM CATALYST

[75] Inventors: Thanikavelu Manimaran; W. Dirk Klobucar; Charles H. Kolich, all of Baton Rouge, La.

[73] Assignee: Ethyl Corporation, Richmond, Va.

[21] Appl. No.: 716,015

[22] Filed: Jun. 17, 1991

[51] Int. Cl.$^5$ .................. C07C 102/00; C07C 63/04; C07C 53/134; C07C 57/30

[52] U.S. Cl. ........................................ 554/35; 556/21; 556/136; 562/493; 562/496

[58] Field of Search .................. 562/493, 496; 556/21, 556/136; 554/35

[56] References Cited

U.S. PATENT DOCUMENTS

| | | | |
|---|---|---|---|
| 3,748,332 | 7/1973 | Wilkinson | 260/270 R |
| 3,793,355 | 2/1974 | Wilkinson | 260/429 R |
| 3,878,122 | 4/1975 | Pennella | 252/411 R |
| 4,268,454 | 5/1981 | Pez et al. | 260/439 R |
| 4,440,936 | 4/1984 | Riley | 562/496 |
| 4,506,030 | 3/1985 | Jones | 502/155 |
| 4,604,474 | 8/1986 | Kumobayashi et al. | 556/7 |
| 4,605,750 | 8/1986 | Kumobayashi et al. | 556/7 |
| 4,691,037 | 9/1987 | Yoshikawa et al. | 556/18 |

OTHER PUBLICATIONS

Tetrahedron: Asymmetry 2(1) 1991, 47 Alcock et al.

*Primary Examiner*—José G. Dees
*Assistant Examiner*—Joseph M. Conrad
*Attorney, Agent, or Firm*—Richard J. Hammond

[57] ABSTRACT

A process for the asymmetric reduction of olefinic amides of the formula

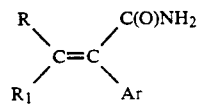

where R and $R_1$ are the same or different and are hydrogen, alkyl, cycloalkyl or haloalkyl and Ar is aryl or substituted aryl is disclosed.

16 Claims, No Drawings

ASYMMETRIC HYDROGENATION OF OLEFINIC AMIDES USING ORGANORUTHENIUM CATALYST

FIELD OF THE INVENTION

This invention relates to a process for the catalytic reduction of aromatic-substituted olefinic amides. More specifically, this invention relates to a process for asymmetrically, catalytically reducing aromatic-substituted olefinic amides using a mixture of an organoruthenium compound and an optically active organophosphorous compound.

BACKGROUND OF THE INVENTION

Enantioselective catalysis using chiral metal complexes provides one of the most general and flexible methods for achieving asymmetric organic reactions. Metallic elements possess a variety of catalytic activities, and permutations of organic ligands or other auxiliary groups directing the steric course of the reaction are practically unlimited. Efficient ligands must be endowed with, for example, suitable functionality, appropriate chirality, a structure capable of differentiating space either electronically or sterically and skeletal rigidity or flexibility.

Among the asymmetric organic reactions catalyzed by chiral transition metal complexes, asymmetric hydrogenation has been one of the best studied, due in large part to the fact that it is the basis for the first commercialized catalytic asymmetric process. See, for example, ApSimon, et al., *Tetrahedron*, 1986, 42, 5157.

Some of the more interesting of the asymmetric hydrogenation catalysts are those derived from BINAP [2,2'-bis(diphenylphosphino)-1,1'-binaphthyl]. See, for example, U.S. Pat. Nos.: 4,691,037; 4,739,084; 4,739,085; 4,764,629; 4,994,607; and 4,766,227. Unlike the more classical models of chira (asymmetric) molecules, chirality in the case of the BINAP-type compounds arises from the restricted rotation about the single bond joining the naphthalene rings. Isomers arising from this type of asymmetry are termed atropisomers.

BINAP-based Ru(II) and Rh(I) complexes induce high enantioselectivity in catalytic reactions. See Noyori and Takaya, *Acc. Chem. Res.*, 1990, 23, 345.

The BINAP ruthenium complexes are dramatically different than the rhodium ones. They have been used to catalyze a variety of asymmetric hydrogenations, including the hydrogenation of enamides and alkyl and aryl-substituted acrylic acids. See Noyori, et al., *Modern Synthetic Methods*, 1989, 5, 115, incorporated herein by reference. Unlike the rhodium catalyzed reductions, ruthenium(II) carboxylate complexes possessing the BINAP ligand are efficient catalysts for the enantioselective hydrogenation of $\alpha,\beta$-unsaturated carboxylic acids. According to Ohta, et al, *J. Org. Chem*, 52, 3174 (1982), the carboxyl moiety of the substrate, and not other oxygen containing groups, is responsible for the stereoselective reaction. Asymmetric reductions of noncarboxyl-containing substrates by ruthenium complexes are inefficient.

The preparation of the BINAP-bearing ruthenium complexes, while not only sophisticated, is time consuming and expensive. Accordingly, it would be advantageous to be able to carry out these enantioselective transformations using more readily prepared catalysts.

In rhodium catalyzed asymmetric reactions, in situ methods of preparing the active catalysts are well established. However, such an in situ method to prepare ruthenium catalysts is not generally successful. See, for example, B. Heiser, et al., *Tetrahedron Asymmetry*, 2, 51 (1991). The necessity of synthesizing the catalyst in an extra step and complications due to catalyst instability are avoided by in situ catalyst generation.

SUMMARY OF THE INVENTION

The present invention involves a novel method for the use of organoruthenium compounds which, when admixed in an appropriate solvent with ligands having optical activity, can be used as in situ catalyst to effect the asymmetric reduction of certain unsaturated organic compounds.

DESCRIPTION OF THE PREFERRED EMBODIMENTS

In the present specification, alkyl means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl, and eicosyl.

Cycloalkyl means cyclic alkyl having 3 to 7 carbon atoms and includes cyclopropyl, cyclobutyl, cyclopentyl, cyclohexyl and cycloheptyl.

Substituted aryl means phenyl or naphthyl substituted by at least one substituent selected from the group consisting of halogen (chlorine, bromine, fluorine or iodine), amino, nitro, hydroxy, alkyl, alkoxy, which means straight or branched chain alkoxy having 1 to 10 carbon atoms, and includes, for example, methoxy, ethoxy, propoxy, isopropoxy, butoxy, isobutoxy, secondary butoxy, tertiary butoxy, pentyloxy, isopentyloxy, hexyloxy, heptyloxy, octyloxy, nonyloxy and decyloxy, haloalkyl which means straight or alkyl having 1 to 8 carbon atoms which is substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl and 2,2,3,3-tetrafluoropropyl.

Haloalkyl means straight or branched chain alkyl having 1 to 10 carbon atoms which is substituted by at least one halogen as mentioned above.

Phenylalkyl means that the alkyl moiety is straight or branched chain alkyl having 1 to 8 carbon atoms and includes, for example, benzyl, 2-phenylethyl, 1-phenylethyl, 3-phenylpropyl, 4-phenylbutyl, 5-phenylpentyl, 6-phenylhexyl and 8-phenyloctyl.

Substituted phenylalkyl means above-mentioned phenylalkyl which is substituted by at least one substituent selected from the group consisting of halogen, amino, nitro, hydroxy, alkyl, alkoxy and haloalkyl on the phenyl nucleus.

Chiral phosphine compound means an optically active alkyl or aryl substituted trivalent phosphorus compound. Examples of such compounds are:

1,2-ethanediyl-bis(o-methoxyphenyl)phenylphosphine (DIPAMP);

N,N'-bis(α-methylbenzyl)-N,N'-bis(diphenylphosphine) ethylenediamine (PNNP);

2,3-bis(diphenylphosphino)butane (CHIRAPHOS);

1,2-bis(diphenylphosphino)propane (PROPHOS);

2,3-O-isopropylidene-2,3-dihydroxy-1,4-bis(diphenylphosphino)butane (DIOP);

2,4-t-butyl 4-(diphenylphosphino)-2-(diphenylphosphinomethyl)-1-pyrrolidine-carboxylate (BPPM);

2,4-bis(diphenylphosphino)pentane (SKEWPHOS);

2,5-bis(diphenylphosphino)hexane (BDPH);

1,2-bis(diphenylphosphino)-1-phenylethane (PHENPHOS);

1,2-bis(diphenylphosphino)-1-cyclohexylethane (CYCPHOS);

α-[1,2-bis(diphenylphosphino)ferrocenyl]-ethyldimethylamine (BPPFA); and trans-4,5-bis[(5H-dibenzophospholyl)methyl]-2,2-dimethyl-1,3-dioxolane (DIPHOL).

A detailed description of suitable phosphines for the present invention is disclosed in "Asymmetric Synthesis", Vol. 5, Ed. by James D. Morrison, Academic Press, Orlando (1985), incorporated herein by reference.

The enantioselective preparations of the present invention are carried out using α-aryl olefinic amides. The olefinic amides have the formula

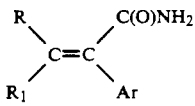

where R and $R_1$ are the same or different and are hydrogen, alkyl, cycloalkyl, or haloalkyl and Ar is aryl or substituted aryl. Preferably R and $R_1$ are the same or different and are hydrogen or alkyl. Most preferred in the above amides is where R and $R_1$ are the same and are hydrogen or methyl. They are reduced (hydrogenated) asymmetrically by a catalytic process employing a mixture of (i) a ruthenium compound and (ii) an optically active ligand such as BINAP in an appropriate solvent where the ligand is

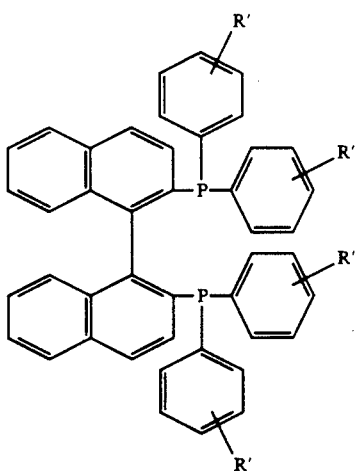

where R' is hydrogen (BINAP), alkyl, haloalkyl, aryl or substituted aryl. It is neither necessary nor economically desirable to isolate the chiral metal catalyst that may be formed in this mixture prior to hydrogenation of the substrate.

The ruthenium compounds of use in this invention may be any of a wide variety of compounds and include, for example, the halides such as ruthenium(III) bromide or ruthenium(III) chloride, mixed halide-chelate complexes such as (cycloocta-1,5-diene)ruthenium(II) chloride polymer, i.e., the chelate complex salts such as illustrated by $[Ru(COD)Cl_2]_n$, or (cycloocta-1,5-diene)ruthenium(II) (2,4-pentanedionate) or ruthenium(III) (2,4pentanedionate). Interestingly, the present invention works well when starting with either Ru(II) or Ru(III) complexes whereas prior art is only effective with Ru(II) species.

The preferred ruthenium compounds of use in the process of the present invention are the chelate complexes of the formula

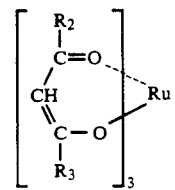

where $R_2$ and $R_3$ are the same or different and are alkyl, aryl, haloalkyl, phenylalkyl or substituted phenylalkyl.

In the preferred ruthenium compound, it is most preferred that $R_2$ and $R_3$ are the same and are alkyl of 1 to 12 carbon atoms having a linear or branched chain. Particularly preferred are where $R_2$ and $R_3$ are the same and are linear or branched $C_1$ to $C_6$ alkyl group. Illustrative alkyl groups most preferably employed as $R_2$ and $R_3$ are methyl, ethyl, propyl, isopropyl, butyl, isobutyl, secondary butyl, tertiary butyl, pentyl, isopentyl, neopentyl, trifluoromethyl and the like.

The chiral organophosphorous compound admixed with the ruthenium compound is preferably one where all R' are the same and are hydrogen or $C_1$ to $C_6$ linear or branched alkyl. Most preferably all R' are the same and are hydrogen, methyl, ethyl, propyl or isopropyl.

The asymmetric catalytic hydrogenations utilizing the catalyst mixture of (i) and (ii) above is mixed with a solution of an α-aryl olefinic amide, typically in a molar ratio of (i):(ii) of 10:1 to 1:10, preferably 8:1 to 1:8, most preferably 1:1.

The molar ratio of (i) to the olefinic amide is between about 1 to 20 to about 1 to 20,000, preferably about 1 to 100 to about 1 to 10,000, most preferably about 1 to 5,000 to about 1 to 10,000.

The combination of the catalyst mixture, the olefinic amide and suitable organic solvent, provide a system suitable for hydrogenation at elevated hydrogen pressure, i.e., pressures above about 75 psig.

To achieve enantioselective hydrogenation of the α-aryl olefinic amide, a mixture of (i) and (ii) in the hydrogenation solvent must be given time (typically 1 to 5 hours) to become activated, either with or without hydrogen pressure at room temperature or at elevated temperature, before the substrate is introduced.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES

Methods (General)

All solvents used in the hydrogenation were reagent grade and were sparged with nitrogen for at least 2 hours to remove oxygen. Conversions were determined by GC (area %); optical purities were determined by HPLC using a chiral column. The metal reactors used were constructed of Monel 400.

Preparation of (S-BINAP)Ruthenium(II)Diacetate

The material was made by the method of T. Ohta, H. Takaya and R. Noyori, *Inorg. Chem.*, 1988, 27, 566.

Example 1

The starting ruthenium(III) (2,4-pentanedionate) and S-BINAP were weighed and combined in a 25 ml flask in a nitrogen-filled glove box. The mixture was transferred to the high pressure reactor using 30 ml of methanol. The reactor was flushed with hydrogen ($3\times300$ psi), warmed to 60° C. and then stirred at 1000 psi ($H_2$) for 3 hr. The reactor was cooled to ambient temperature and then vented. A solution of 2-(4-isobutylphenyl)acrylamide (UAM) in 10 ml of methanol was added to the reactor. After flushing ($3\times300$ psi $H_2$) and sealing the vessel under 1000 psi hydrogen, the mixture was stirred (600 rpm) and sampled for GC analyses as shown in the Table. After 3 hours at 24° C., the hydrogenation was complete. The saturated amide product was hydrolyzed to ibuprofen as described below. The optical purity of the S-ibuprofen hydrolysis product was 71% by HPLC.

Example 2

The starting Ru(acac)$_3$ and S-BINAP were weighed and combined in a 25 ml flask in a nitrogen-filled glove box. The mixture was transferred to the high pressure reactor using 30 ml of methanol. The reactor was flushed with hydrogen ($3\times300$ psi) and then stirred with 1000 psi ($H_2$) at 25° C. for 4 hr. The reactor was vented, and a solution of UAM in 10 ml of methanol was added to the reactor. After flushing ($3\times300$ psi $H_2$) and sealing the vessel under 1000 psi hydrogen, the mixture was stirred (600 rpm) and sampled for GC analses as shown in the Table. The reaction was complete in 19 hours at 25° C. After hydrolysis of the amide to ibuprofen, HPLC analysis indicated an optical purity of 68%.

Example 3

The Ru(S-BINAP)(OAc)$_2$ catalyst and UAM were weighed out and combined in a 25 ml flask in a nitrogen-filled glove box. The mixture was transferred to the high pressure reactor using 40 ml of methanol. The reactor was flushed with $H_2$ ($3\times300$ psi) and then sealed under 1000 psi $H_2$. The mixture was stirred (300 rpm) at 23° C. for 20 hours to complete the hydrogenation. After hydrolysis to ibuprofen, HPLC analysis indicated an optical purity of 70%.

Hydrolysis of the Amides to Ibuprofen

Methanol was removed from the hydrogenation reaction mixture at reduced pressure on a rotary evaporator. To the resultant solid was added 5 ml of concentrated hydrochloric acid. This reaction mixture was stirred for 4 hours at 110° C. under nitrogen. After cooling, the reaction mixture was extracted with diethyl ether ($4\times10$ ml). The ether solution of ibuprofen was analyzed by HPLC to determine the optical purity.

The above hydrolysis procedure gives about 2% racemization demonstrated by: (1) converting a sample of (S)-(+)-ibuprofen (98.6% S enantiomer by HPLC) to (S)-(+)-2-(4-isobutylphenyl)propanoyl chloride with oxalyl chloride; (2) treating the chloride with ammonia to obtain (S)-(+)-2-(4-isobutylphenyl)propionamide; and (3) hydrolyzing the amide as described above to regenerate (S)-(+)-ibuprofen (96.6% S enantiomer by HPLC).

TABLE I

| | UAM HYDROGENATION RESULTS (900–1000 psi H$_2$ in Methanol) | | | | |
|---|---|---|---|---|---|
| | | CATALYST STOICHIOMETRY (mmol) | | TEMP/TIME | CONVERSION | |
| EXAMPLE | SUBSTRATE (mmol) | METAL COMPLEX | PHOS. LIGAND | (°C./hr) | (GC Area %) | % ee |
| 1 | UAM (1.12) | Ru(acac)$_3$ (0.063) | S—BINAP (0.072) | 24/0.5 | 31 | |
| | | | | 24/1 | 48 | |
| | | | | 24/2 | 84 | |
| | | | | 24/3 | 100 | 71(S) |
| 2 | UAM (1.15) | Ru(acac)$_3$ (0.060) | S—BINAP (0.058) | 25/2.3 | 16 | |
| | | | | 25/19 | 100 | 68(S) |
| 3 | UAM (1.07) | Ru(S—BINAP)(OAc)$_2$ (0.023) | None | 23/20 | 100 | 70(S) | acac = 2,4-pentanedionate
BINAP = 2,2'-bis(diphenylphosphino)-1,1'-binaphthyl
OAc = acetate
UAM = 2-[4-isobutylphenyl]acrylamide
ee = enantiomeric excess (optical purity)

We claim:

1. A process for preparing optically active α-aryl aliphatic amides which comprises catalytically, asymmetrically hydrogenating an olefinic amide of the formula

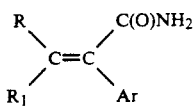

where R and R₁ are the same or different and are hydrogen, alkyl, cycloalkyl, or haloalkyl; and Ar is aryl or substituted aryl; by utilizing a mixture of (i) a ruthenium compound of the formula

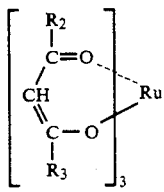

where R₂ and R₃ are the same or different and are alkyl, haloalkyl, aryl, substituted aryl, phenylalkyl or substituted phenylalkyl; and (ii) a chiral phosphine compound.

2. The process of claim 1 wherein R and R₁ are the same or different and are hydrogen or alkyl.

3. The process according to claim 2 wherein R and R₁ are hydrogen.

4. The process according to claim 1 wherein Ar is phenyl or naphthyl substituted with alkyl or alkoxy.

5. The process according to claim 4 wherein Ar is phenyl substituted with methyl, ethyl, n-propyl or isobutyl.

6. The process according to claim 1 wherein R₂ and R₃ are the same and are alkyl.

7. The process according to claim 6 wherein R₂ and R₃ are methyl.

8. A process for preparing optically active α-aryl aliphatic carboxylic acids which comprises catalytically, asymmetrically hydrogenating an olefinic amide of the formula

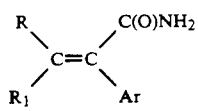

where R and R₁ are the same or different and are hydrogen, alkyl, cycloalkyl, or haloalkyl; and Ar is aryl or substituted aryl; by utilizing a mixture of (i) a ruthenium compound of the formula

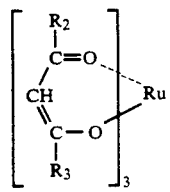

where R₂ and R₃ are the same or different and are alkyl, phenylalkyl or substituted phenylalkyl; and (ii) an optically active ligand having the structure

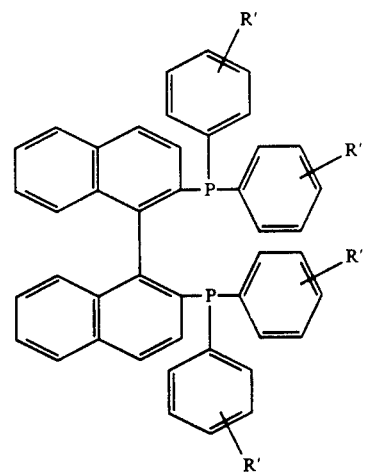

where R' is hydrogen, alkyl, haloalkyl, aryl or substituted aryl; and hydrolyzing the product of said catalytic asymmetric hydrogenation.

9. The process according to claim 8 wherein said ruthenium compound is a halide, a mixed halide-chelate complex or a chelate complex.

10. The process of claim 8 wherein R and R₁ are the same or different and are hydrogen or alkyl.

11. The process according to claim 10 wherein R and R₁ are hydrogen.

12. The process according to claim 8 wherein Ar is phenyl or naphthyl substituted with alkyl or alkoxy.

13. The process according to claim 12 wherein Ar is phenyl substituted with methyl, ethyl, n-propyl or isobutyl.

14. The process according to claim 8 wherein R₂ and R₃ are the same and are alkyl.

15. The process according to claim 14 wherein R₂ and R₃ are methyl.

16. A process for preparing S-ibuprofen which comprises: (1) catalytically, asymmetrically hydrogenating 2-(4-isobutylphenyl)acrylamide by utilizing a mixture of

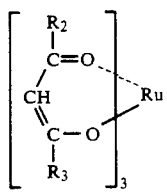

and S-BINAP, where R₂ and R₃ are the same or different and are alkyl and BINAP is

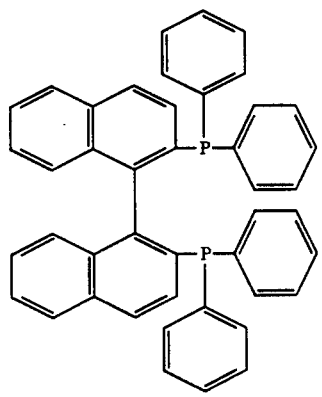

and (2) hydrolyzing the product of step (1).

* * * * *